US006284520B1

(12) United States Patent
Meyhack et al.

(10) Patent No.: US 6,284,520 B1
(45) Date of Patent: *Sep. 4, 2001

(54) PROCESS FOR THE PRODUCTION OF PROTEINS

(75) Inventors: Bernd Meyhack, Magden (CH); Michael Bröker, Marburg (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/305,723

(22) Filed: May 5, 1999

Related U.S. Application Data

(63) Continuation of application No. 08/875,802, filed as application No. PCT/EP96/00314 on Jan. 26, 1996, now Pat. No. 5,981,227.

(30) Foreign Application Priority Data

Feb. 9, 1995 (DE) .................................................. 95810084

(51) Int. Cl.[7] .............................. C12N 1/19; C12N 15/81
(52) U.S. Cl. .................................. 435/254.21; 435/320.1; 435/69.1; 435/69.2; 435/69.51; 435/69.7; 435/254.11; 435/254.2
(58) Field of Search ............................... 435/320.1, 69.1, 435/252.3, 254.11, 254.21, 254.2

(56) References Cited

U.S. PATENT DOCUMENTS

| 5,089,400 | 2/1992 | Meyer | 435/69.51 |
| 5,955,090 | * 9/1999 | Knapp et al. | 424/260.1 |
| 5,981,227 | * 11/1999 | Meyhack et al. | 435/69.1 |

FOREIGN PATENT DOCUMENTS

| 0 076 489 | 4/1983 | (EP) . |
| 0 143 081 | 5/1985 | (EP) . |
| 0 205 404 | 12/1986 | (EP) . |
| 0 225 633 | 6/1987 | (EP) . |
| 0 278 696 | 8/1988 | (EP) . |
| 0 352 060 | 7/1989 | (EP) . |
| 0 340 986 | 11/1989 | (EP) . |
| 0 341 215 | 11/1989 | (EP) . |
| 0 439 997 | 8/1991 | (EP) . |
| WO 90/05184 | 5/1990 | (WO) . |

OTHER PUBLICATIONS

Anatalis T.M. et al., PNAS USA, vol. 85, "Cloning and expression of a cDNA coding for a human monocyte–derived plasminogen activator inhibitor," pp. 985–989 (1988).

Baldari C. et al., The EMBO Journal, vol. 6(1), "A novel leader peptide which allows efficient secretion of a fragment of human interleukin 1β in Saccharomyces cerevisiae," pp. 229–234 (1987).

Cesareni, G. and Murray J., Genetic Engineering, vol. 4, "Plasmid Vectors Carrying the Replication Origin in Filamentous Single–Stranded Phages," pp. 135–154 (1989).

Erhart e. and Hollenberg C.j The Journal of Bacteriology, vol. 156 (2), "The Presence of a Defective LEU2 Gene on 2μ DNA Recombinant Plasmids of Saccharomyces cerevisiae Is Responsible for Curing and High Copy Number," pp. 625–625 (1983).

George–Nascimento C. et al., Biochemistry, vol. 27, "Characterization of Recombinant Human Epidermal Growth Factor Produced in Yeast," pp. 797–802 (1988).

Guarente L., PNAS USA, vol. 79, "A GAL10–CYC1 hybrid yeast promoter identifies the GAL4 regulatory region as an upstream site," pp. 7410–7414 (1982).

Heinemeyer W. et al., EMBO Journal, vol. 10(3), "Proteinase yscE, the yeast proteasome/multi–catalytic–multifunctional proteinase: mutants unravel its function in stress induced proteolysis and uncover its necessity for cell survival," pp. 555–562 (1991).

Henco K. et al., Journal of Molecular Biology, vol. 185, "Structural Relationship of Human Interferon Alpha Genes and Pseudogenes," pp. 227–260 (1985).

Hinnen, A. et al., PNAS USA, vol. 75 (4), "Transformation of yeast," pp. 1929–1933 (1978).

Hinnen A. et al., "Heterologous Gene Expression in Yeast," in *Yeast Genetic Engineering,* Barr et al. (Eds.), Butterworths, Boston, pp. 193–213 (1989).

Hitzeman, R. et al., Nature, vol. 293, "Expression of a human gene for interferon in yeast," pp. 717–722 (1981).

Knecht R. and Chang J.–Y., Anal. Chem., vol. 58, "Liquid Chromatographic Determination of Amino Acids after Gas–Phase Hydrolysis and Derivatization with (Dimethylamino)azobenzenesulfonyl Chloride," pp. 2375–2379 (1986).

Price V. et al., Gene, vol. 55, "Expression, purification and characterization of recombinant murine granulocyte–macrophage colony–stimulating factor and bovine interleukin–2 from yeast," pp. 287–293 (1987).

Rubinstein S. et al., Journal of Virology, vol. 37 (2), "Convenient Assay for Interferons," pp. 755–758 (1981).

(List continued on next page.)

*Primary Examiner*—David Guzo
(74) *Attorney, Agent, or Firm*—George R. Dohmann

(57) ABSTRACT

The invention pertains to the field of recombinant DNA technology and concerns a method for the production of a protein heterologous to yeast in a homogenous form with the aid of *Saccharomyces cerevisiae* strain HT393 or a derivative thereof carrying a hybrid vector containing the genes for said protein.

12 Claims, 3 Drawing Sheets

OTHER PUBLICATIONS

Rudolph H. et al., Cell, vol. 58, "The Yeast Secretory Pathway Is Perturbed by Mutations in PMR1, a Member of a $Ca^{2+}$ATPase Family," pp. 133–145 (1983).

Russell D. and Smith M., The Journal of Biological Chemistry, vol. 258 (4), "Nucleotide Sequence of the Yeast Alcohol Dehydrogenase II Gene," pp. 2674–2682 (1983).

Stanssens P. et al., Nucleic Acids Research, vol. 17 (12), "Efficient oligonucleotide–directed construction of mutations in expression vectors by the gapped duplex DNA method using alternating selectable markers," pp. 4441–4454 (1989).

Vlasuk G., The Journal of Biological Chemistry, vol. 261 (11), "Expression and Secretion of Biologically Active Human Atrial Natriuretic Peptide in *Saccharomyces cerevisiae*," pp. 4789–4796 (1986).

* cited by examiner

SEQUENCE LISTING

<160> NUMBER OF SEQ ID NOS: 6

<210> SEQ ID NO 1
<211> LENGTH: 1566
<212> TYPE: DNA
<213> ORGANISM: Artificial Sequence
<220> FEATURE:
<221> NAME/KEY: misc_feature
<222> LOCATION: (2)..(277)
<223> OTHER INFORMATION: /function=pBR322 SalI-BamHI fragment
<221> NAME/KEY: promoter
<222> LOCATION: (278)..(810)
<223> OTHER INFORMATION: /phenotype=PHO5 promoter position -541 to -8
<221> NAME/KEY: misc_feature
<222> LOCATION: (811)..(820)
<223> OTHER INFORMATION: /function= EcoRI linker
<221> NAME/KEY: CDS
<222> LOCATION: (821)..(1324)
<223> OTHER INFORMATION: /product=alpha interferon B/D including Met
<221> NAME/KEY: misc_feature
<222> LOCATION: (1325)..(1380)
<223> OTHER INFORMATION: /function= interferon 3' non-coding sequence
<221> NAME/KEY: terminator
<222> LOCATION: (1381)..(1566)
<223> OTHER INFORMATION: /standard name=linker and PHO5 terminator
<223> OTHER INFORMATION: Description of Artificial Sequence:recombinant
      alpha interferon B/D with promoter and terminator
      sequences -continued

```
<400> SEQUENCE: 1
gtcgacgctc tcccttatgc gactcctgca ttaggaagca gcccagtagt aggttgaggc      60
cgttgagcac cgccgccgca aggaatggtg catgcaagga gatggcgccc aacagtcccc     120
cggccacggg gcctgccacc atacccacgc cgaaacaagc gctcatgagc ccgaagtggc     180
gagcccgatc ttcccatcg gtgatgtcg cgatataggc gccagcaacc gcacctgtgg      240
cgccggtgat gccggccacg atgcgtccgg cgtagaggat ccgaaagttg tattcaacaa     300
gaatgcgcaa atatgtcaac gtatttggaa gtcatcttat gtgcgctgct ttaatgtttt     360
ctcatgtaag cggacgtcgt ctataaactt caaacgaagg taaaggttc atagcgcttt      420 ttctttgtct gcacaaagaa atatatatta aattagcacg ttttcgcata gaacgcaact     480
gcacaatgcc aaaaaagta aaagtgatta aaagagttaa ttgataggc aatctctaaa       540 tgaatcgata caaccttggc actcacacgt gggactagca cagactaaat ttatgattct     600
ggtccctgtt ttcgaagaga tcgcacatgc caaattatca aattggtcac cttacttggc     660
aaggcatata cccatttggg ataagggtaa acatctttga attgtcgaaa tgaaacgtat     720
ataagcgctg atgttttgct aagtcgaggt tagtatggct tcatctctca tgagaataag     780
aacaacaaca aatagagcaa gcaaattcga gaattcgaca atg tgt gat ctg cct      835
                                              Met Cys Asp Leu Pro
                                                1               5 cag act cac agc ctg ggt aac agg agg gcc ttg ata ctc ctg gca caa      883
Gln Thr His Ser Leu Gly Asn Arg Arg Ala Leu Ile Leu Leu Ala Gln
              10                  15                  20 atg cga aga atc tct cct ttc tcc tgc ctg aag gac aga cat gac ttt      931
Met Arg Arg Ile Ser Pro Phe Ser Cys Leu Lys Asp Arg His Asp Phe
          25                  30                  35 gaa ttc ccc cag gag gag ttt gat gat aaa cag ttc cag aag gct caa      979
Glu Phe Pro Gln Glu Glu Phe Asp Asp Lys Gln Phe Gln Lys Ala Gln
      40                  45                  50 gcc atc tct gtc ctc cat gag atg atc cag cag atc ttc aac ctc ttt     1027
Ala Ile Ser Val Leu His Glu Met Ile Gln Gln Ile Phe Asn Leu Phe
 55                  60                  65 acc aca aaa gat tca tct gct gct tgg gat gag gac ctc cta gac aaa     1075
Thr Thr Lys Asp Ser Ser Ala Ala Trp Asp Glu Asp Leu Leu Asp Lys
 70                  75                  80                  85 ttc tgc acc gaa ctc tac cag cag ctg aat gac ctg gag tcc tgt gtg     1123
Phe Cys Thr Glu Leu Tyr Gln Gln Leu Asn Asp Leu Glu Ser Cys Val
                 90                  95                 100 atg cag gaa gtg ggg gtg ata gag tct ccc ctg atg tac gag gac tcc     1171
Met Gln Glu Val Gly Val Ile Glu Ser Pro Leu Met Tyr Glu Asp Ser
             105                 110                 115 atc ctg gct gtg agg aaa tac ttc caa aga atc act cta tat ctg aca     1219
Ile Leu Ala Val Arg Lys Tyr Phe Gln Arg Ile Thr Leu Tyr Leu Thr
         120                 125                 130 gag aag aaa tac agc tct tgt gcc tgg gag gtt gtc aga gca gaa atc     1267
Glu Lys Lys Tyr Ser Ser Cys Ala Trp Glu Val Val Arg Ala Glu Ile
     135                 140                 145 atg aga tcc ttc tct tta tca atc aac ttg caa aaa aga ttg aag agt     1315
Met Arg Ser Phe Ser Leu Ser Ile Asn Leu Gln Lys Arg Leu Lys Ser
150                 155                 160                 165 aag gaa tga gacctggtac aaacacggaaa tgattcttat agactaatac            1364
Lys Glu agcagctcac acttcgtcga gggtcagcag cgtcagtaac tctactgaat tgaccttcta   1424
ctgggactgg aacactactc attacaacgc cagtctattg agacaatagt tttgtataac   1484
```

```
taaataatat tggaaactaa atacgaatac ccaaattttt tatctaaatt ttgccgaaag    1544
attaaaatct gcagccaagc tt                                             1566
```

<210> SEQ ID NO 2
<211> LENGTH: 167
<212> TYPE: PRT
<213> ORGANISM: Artificial Sequence
<220> FEATURE:
<223> OTHER INFORMATION: Description of Artificial Sequence:recombinant
      alpha-interferon B/D

<400> SEQUENCE: 2

```
Met Cys Asp Leu Pro Gln Thr His Ser Leu Gly Asn Arg Arg Ala Leu
 1               5                  10                  15

Ile Leu Leu Ala Gln Met Arg Arg Ile Ser Pro Phe Ser Cys Leu Lys
                20                  25                  30

Asp Arg His Asp Phe Glu Phe Pro Gln Glu Glu Phe Asp Asp Lys Gln
            35                  40                  45

Phe Gln Lys Ala Gln Ala Ile Ser Val Leu His Glu Met Ile Gln Gln
        50                  55                  60

Ile Phe Asn Leu Phe Thr Thr Lys Asp Ser Ser Ala Ala Trp Asp Glu
 65                  70                  75                  80

Asp Leu Leu Asp Lys Phe Cys Thr Glu Leu Tyr Gln Gln Leu Asn Asp
                 85                  90                  95

Leu Glu Ser Cys Val Met Gln Glu Val Gly Val Ile Glu Ser Pro Leu
            100                 105                 110

Met Tyr Glu Asp Ser Ile Leu Ala Val Arg Lys Tyr Phe Gln Arg Ile
        115                 120                 125

Thr Leu Tyr Leu Thr Glu Lys Lys Tyr Ser Ser Cys Ala Trp Glu Val
    130                 135                 140

Val Arg Ala Glu Ile Met Arg Ser Phe Ser Leu Ser Ile Asn Leu Gln
145                 150                 155                 160

Lys Arg Leu Lys Ser Lys Glu
                165
```

<210> SEQ ID NO 3
<211> LENGTH: 167
<212> TYPE: PRT
<213> ORGANISM: Artificial Sequence
<220> FEATURE:
<223> OTHER INFORMATION: Description of Artificial Sequence:recombinant
      alpha-interferon B/D

<400> SEQUENCE: 3

```
Met Cys Asp Leu Pro Gln Thr His Ser Leu Gly Asn Arg Arg Ala Leu
 1               5                  10                  15

Ile Leu Leu Ala Gln Met Arg Arg Ile Ser Pro Phe Ser Cys Leu Lys
                20                  25                  30

Asp Arg His Asp Phe Glu Phe Pro Gln Glu Glu Phe Asp Asp Lys Gln
            35                  40                  45

Phe Gln Lys Ala Gln Ala Ile Ser Val Leu His Glu Met Ile Gln Gln
        50                  55                  60

Ile Phe Asn Leu Phe Thr Thr Lys Asp Ser Ser Ala Ala Trp Asp Glu
 65                  70                  75                  80

Asp Leu Leu Asp Lys Phe Cys Thr Glu Leu Tyr Gln Gln Leu Asn Asp
                 85                  90                  95

Leu Glu Ser Cys Val Met Gln Glu Val Gly Val Ile Glu Ser Pro Leu
            100                 105                 110
```

```
Met Tyr Glu Asp Ser Ile Leu Ala Val Arg Lys Tyr Phe Gln Arg Ile
        115                 120                 125
Thr Leu Tyr Leu Thr Glu Lys Lys Tyr Ser Ser Cys Ala Trp Glu Val
    130                 135                 140
Val Arg Ala Glu Ile Met Arg Ser Phe Ser Leu Ser Ile Asn Leu Gln
145                 150                 155                 160
Lys Arg Leu Lys Ser Lys Glu
                165

<210> SEQ ID NO 4
<211> LENGTH: 166
<212> TYPE: PRT
<213> ORGANISM: Artificial Sequence
<220> FEATURE:
<221> NAME/KEY: PEPTIDE
<222> LOCATION: (1)..(166)
<223> OTHER INFORMATION: product=alpha interferon B/D
<223> OTHER INFORMATION: Description of Artificial Sequence:alpha
      interferon B/D without amino Met

<400> SEQUENCE: 4

Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
            20                  25                  30
Arg His Asp Phe Glu Phe Pro Gln Glu Glu Phe Asp Asp Lys Gln Phe
        35                  40                  45
Gln Lys Ala Gln Ala Ile Ser Val Leu His Glu Met Ile Gln Gln Ile
    50                  55                  60
Phe Asn Leu Phe Thr Thr Lys Asp Ser Ser Ala Ala Trp Asp Glu Asp
65                  70                  75                  80
Leu Leu Asp Lys Phe Cys Thr Glu Leu Tyr Gln Gln Leu Asn Asp Leu
                85                  90                  95
Glu Ser Cys Val Met Gln Glu Val Gly Val Ile Glu Ser Pro Leu Met
            100                 105                 110
Tyr Glu Asp Ser Ile Leu Ala Val Arg Lys Tyr Phe Gln Arg Ile Thr
        115                 120                 125
Leu Tyr Leu Thr Glu Lys Lys Tyr Ser Ser Cys Ala Trp Glu Val Val
    130                 135                 140
Arg Ala Glu Ile Met Arg Ser Phe Ser Leu Ser Ile Asn Leu Gln Lys
145                 150                 155                 160
Arg Leu Lys Ser Lys Glu
                165

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:ADR2
      promoter
<221> NAME/KEY: promoter
<222> LOCATION: (1)..(12)
<223> OTHER INFORMATION: portion of ADR2 promoter with BamHI and SalI
      sites

<400> SEQUENCE: 5
ggatccgtcg acatg                                                    15

<210> SEQ ID NO 6
```

-continued

```
<211> LENGTH: 23
<212> TYPE: DNA
<213> ORGANISM: Artificial Sequence
<220> FEATURE:
<223> OTHER INFORMATION: Description of Artificial Sequence:EcoRI/DdeI
      linker
<221> NAME/KEY: misc_feature
<222> LOCATION: (1)..(23)
<223> OTHER INFORMATION: EcoRI/DdeI linker for ligation to PHO5 promoter

<400> SEQUENCE: 6
aattcgacaa tgtgtgatct gcc                                            23
```

PROCESS FOR THE PRODUCTION OF PROTEINS

This application is a continuation application of U.S. patent application Ser. No. 08/875,802, filed Oct. 17, 1997 entitled "Process for the Production of Proteins" and issued as U.S. Pat. No. 5,981,227, which is a 371 application of PCT/EP96/00314, filed Jan. 26, 1996.

The invention pertains to the field of recombinant DNA technology and concerns a method for the production of proteins with the aid of genetically engineered yeast cells carrying hybrid vectors comprising the genes for said proteins.

BACKGROUND OF THE INVENTION

Although in genetic engineering numerous protein expression systems for prokaryotic and eukaryotic hosts are already known, there is a continuing demand for novel systems which have advantages over the known systems.

Working on the expression of heterologous proteins in the baker yeast *Saccharomyces cerevisiae*, it has been commonly observed, that a high-level expression is dependent on many factors, e.g. plasmid stability, plasmid copy number, promoter strength, translation efficiency, low protein degradation.

In this context, one of the very important requisites is the yeast strain which is used for the production.

Recently, quite a number of heterologous proteins have been expressed in different yeast strains after transformation of yeast cells with suitable expression vectors comprising DNA sequences coding for said proteins, like e.g. α-interferon (Hitzeman et al. Nature (1981), 293, 717–722), tissue-type plasminogen activator (EP-A-143081) or certain desulfatohirudins (EP-A-225633). In many cases, however, the heterologous proteins are not synthesized in pure form, but as a mixture containing partially degraded such as C- or N-terminally shortened proteins. For instance, the expression of human atrial natriuretic peptide (hANP) in yeast resulted in the secretion of two forms of mature hANP differing in their C-terminus (Vlasuk et al. J. Biol. Chem. (1986), 261, 4789–4796). Similar results have been obtained after the expression of epidermal growth factor (EGF) in yeast (George-Nascimento et al. Biochemistry (1988), 27, 797–802) where the secreted expression products were heterologous in that either the last (Arg 53) or the last two amino acids (Leu 52 and Arg 53) were missing and no full-length EGF was produced.

The separation of mixtures containing full-length proteins such as α-interferon, tissue-type plasminogen activator, inhibitors of tissue-type plasminogen activator, or desulfatohirudins as well as partially degraded like C- or N-terminally shortened derivatives thereof into the individual components and the purification of these components to homogeneity, if these derivatives are biologically active at all, is laborious and time-consuming. Considering the incidental expenses there is a need for improved methods which render possible the economic production of homogenous proteins such as desulfatohirudin in yeast. It is an object of the present invention to provide methods for the production of proteins heterologous to yeast in a homogenous form.

Surprisingly it has been found, that the use of *Saccharomyces cerevisiae* strain HT393 for the expression of heterologous proteins leads to increased yield of biologically active and undegraded form of the expressed heterologous protein, compared to other *Saccharomyces cerevisiae* strains that are genetically closely related, e.g., to strain cl3-ABYS-86 (DSM 9698) that is genetically closest related.

DESCRIPTION OF THE INVENTION

The present invention concerns a process for the production of a protein heterologous to yeast in a homogenous form characterized in that *Saccharomyces cerevisiae* strain HT393 (DSM 9697) or a derivative thereof is used for the expression of said heterologous protein.

In a preferred embodiment, the present invention relates to an improved process for the production of a protein heterologous to yeast in a homogenous form comprising culturing *Saccharomyces cerevisiae* strain HT393 (DSM 9697) or a derivative thereof that has been transformed with a hybrid vector comprising a DNA sequence coding for said heterologous protein and isolating said heterologous protein.

A derivative of HT393 is a strain that is derived from HT393 and shows the same properties in respect to the production of heterologous proteins. The use of the inventive strains leads, e.g., to an increased yield of a biologically active and undegraded form of an expressed heterologous protein.

This heterologous protein can also be processed further, e.g. glycosylated. Useful proteins are, for example, enzymes that can be used, for the production of nutrients and for performing enzymatic reactions in chemistry, or proteins which are useful and valuable as nutrients or for the treatment of human or animal diseases or for the prevention thereof, for example hormones, polypeptides with immunomodulatory, anti-viral and anti-tumor properties, antibodies, viral antigens, vaccines, clotting factors, enzyme inhibitors, foodstuffs and the like.

Such heterologous structural genes are for example those coding for hormones such as secretin, thymosin, relaxin, calcitonin, luteinizing hormone, parathyroid hormone, adreno adenocorticotropin, melanoycte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFα or TGFβ, e.g. TGFβ1, β2 or β3, growth hormone, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, inhibitors such as proteinase inhibitors such as $α_1$-antitrypsin, SLPI, an inhibitor of the plasminogen activator (PAI-2) and the like, hepatitis virus antigens, such as hepatitis B virus surface or core antigen or hepatitis A virus antigen, or hepatitis nonA-nonB antigen, plasminogen activators, such as tissue plasminogen activator or urokinase, tumor necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, e.g. sCD23 and the like, calcitonin, human calcitonin-related peptide, blood clotting factors, such as factor IX or VIIIc, erythropoietin, eglin, such as eglin C, desulfatohirudin, such as desulfatohirudin variant HV1, HV2 or PA, human superoxide dismutase, viral thymidin kinase, β-lactamase, glucose isomerase.

Preferred genes are those coding for a human α-interferon or hybrid interferon, particularly hybrid interferon BDBB and an inhibitor of the plasminogen activator (PAI-2).

In a preferred embodiment of the invention, the expressed heterologous protein is not secreted.

S. cerevisiae strain HT 393 (E95-1-2A) is obtained from strain cl3-ABYS-86 (DSM 9698) as described in Heinemeyer et al, EMBO J. (1991), 10, 555–562.

The wording derivatives of S. cerevisiae strain HT 393 embraces strains that are derived by genetic engineering from HT 393 and are, e.g., strains that are additionally cleared from two-micron (2μ) DNA (cir°), have a different mating type (MATα) and/or different selection marker. Preferred is HT 393 and derivatives thereof that are also deficient for protease A, protease B, carboxypeptidase Y, carboxypeptidase S and proteinase yscE.

Essentially preferred are HT 393 and derivatives thereof that show at least the following genetic characterization MATa, leu2-3, leu2-112, ura3Δ5, prb1-1, cps1-3, prc1-1, pra1-1 and pre1-1.

Expression Cassettes

A suitable expression cassette comprises a promoter operably linked to a DNA sequence coding for the protein and to a DNA sequence containing transcription termination signals.

The expression cassette may additionally comprise a DNA sequence encoding a signal peptide linked in the proper reading frame to the DNA sequence coding for the inventive protein.

In a preferred embodiment, the promoter, the signal sequence, if present, and the terminator are recognized by the yeast expression system.

Promoter suitable for expression in a certain host are well known. Examples are the promoter of the TRP1 gene, the ADC1 gene (coding for the alcohol dehydrogenase I) or ADR2 gene (coding for the alcohol dehydrogenase II), acid phosphatase (PHO5) gene, CUP1 gene, isocytochrome c gene, or a promoter of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes, a promoter of the yeast mating pheromone genes coding for the a- or α-factor, or the GAL/CYC1 hybrid promoter (intergenic region of the GAL1-GAL10 gene/Cytochrome1 gene; Guarente et al. Proc. Natl. Acad. Sci. (1982), 79, 7410–7414). Preferred vectors of the present invention contain, e.g., promoters with transcriptional control that can be turned on or off by variation of the growth conditions, e.g. the PHO5, the ADR2, or the GAL/CYC1 promoter. For example, the PHO5 promoter can be repressed or derepressed at will, solely by increasing or decreasing the concentration of inorganic phosphate in the medium.

The DNA sequence encoding a signal peptide ("signal sequence"), e.g. a yeast signal peptide, is derived, e.g., from a yeast gene, coding for a protein which is ordinarily secreted. Yeast signal sequences are, for example, the signal sequences of the yeast invertase (SUC2), α-factor, pheromone peptidase (KEX1), "killer toxin" and repressible acid phosphatase (PHO5) genes and the glucoamylase signal sequence from Aspergillus awamori. Additional sequences, such as pro- or spacer-sequences which may carry specific processing signals can also be included in the constructions to facilitate accurate processing of precursor molecules. For example, the processing signals contain a Lys-Arg residue, which is recognized by a yeast endopeptidase located in the Golgi membranes.

A DNA sequence containing transcription termination signals, e.g. yeast transcription termination signals, is preferably the 3' flanking sequence of a gene, e.g. a yeast gene, which contains proper signals for transcription termination and polyadenylation. The preferred flanking sequence is that of the yeast PHO5, the FLP and the α-factor gene.

The DNA coding for the protein according to the invention may be isolated from a gene bank of the natural host by methods known in the art like excision of the desired fragment using suitable restriction enzymes, PCR or may be synthesized chemically, using, e.g., the preferred codon usage of the host.

The promoter, the DNA sequence coding for the protein and the DNA sequence containing transcription termination signals are operably linked to each other, i.e. they are juxtaposed in such a manner that their normal functions are maintained. The array is such that the promoter effects proper expression of the protein or, if a signal sequence is present, the signal sequence-protein complex; the transcription termination signals effect proper termination of transcription and polyadenylation. In case a signal sequence is used, the signal sequence is linked in the proper reading frame to the protein gene in such a manner that the last codon of the signal sequence is directly linked to the first codon of the gene for the protein. The signal sequence, if present, has its own ATG for translation initiation. The junction of these sequences may, for example, be effected by means of synthetic oligodeoxynucleotide linkers carrying the recognition sequence of an endonuclease. Examples for related expression cassettes are described e.g. in EP-A-341215.

Preferred expression cassettes comprise the PHO5, the ADR2, or the GAL/CYC1 promoter, the DNA coding for a protein as defined above and the PHO5, α-factor or FLP terminator.

Especially preferred are expression cassettes as comprised, for example in pPAI-2A-10, pPAI-2A-20, pPAI-2B-10, pPAI-2B-20, or in SEQ ID NO:1 or a functional fragment or derivative thereof.

A functional fragment or derivative of said recombinant DNA molecule is, for example, a fragment coding for a shortened or elongated version of a above mentioned protein or an expression cassette containing a recombinant DNA molecule coding for said protein.

Recombinant Plasmids

The expression cassette as described above are normally inserted in a plasmid, suitable for expression of heterologous proteins in yeast. These plasmids are based, i.e., on the two-micron, pMB354 or the pEMBLyex plasmids (Cesareni and Murray, Genetic Engineering (1989), 4, 135–154). Suitable recombinant plasmids contain, for example, apart from the protein expression cassette, a DNA segment originating from two-micron DNA containing the origin of replication or total two-micron DNA. For example, plasmids according to the invention contain the complete two-micron DNA in an uninterrupted form, i.e. two-micron DNA is cleaved once with a restriction endonuclease, the linearized DNA is linked with the other components of the vector prior to recircularization. The restriction site is chosen such that normal function of the REP1, REP2 and FLP genes and of the ORI, STB, IR1 and IR2 sites of two-micron DNA as well as small "FLP recognition target" (FRT) sites, located near the center of each inverted repeat (IR) at which the FLP recombinase acts, are maintained. Optionally, the restriction site is chosen such that the D gene of two-micron DNA is kept intact too. Suitable restriction sites are, for example, the unique HpaI and SnaBI sites located outside of all of said genes and sites. However, it is likewise possible to insert the expression cassette and further components (cf. below) at different (such as two) restriction sites, especially those mentioned above, within two-micron DNA.

Such a plasmid derivative may comprise two invertedly repeated FRT sites or an additional, third FRT site. The former kind of plasmid is hereinafter called a "symmetric two-micron-like hybrid vector". The latter kind of plasmid is hereinafter called "symmetric two-micron-like disintegration vector" despite it is not a real symmetric plasmid but gives rise to a symmetric two-micron-like hybrid vector in the yeast cell transformed therewith.

A symmetric two-micron-like hybrid vector of the invention does preferentially not contain bacterial or viral DNA sequences, i.e. DNA derived from a bacterial genome, plasmid or virus. However, a two-micron-like disintegration vector of the invention may comprise DNA sequences of prokaryotic origin between the two directly repeated FRT sites which are excised from the vector in the transformed yeast cell in which the symmetric two-micron-like hybrid vector is generated from the disintegration vector. These DNA sequences are bacterial sequences as described below and can provide to the vector essential structural or functional features or can also only have the function of filling up the two regions between the two invertedly repeated FRT sites of an unsymmetric two-micron-like plasmid derivative or of an "unsymmetric" disintegration vector in order to construct a symmetric two-micron-like hybrid vector or a symmetric disintegration vector.

Preferably, the expression plasmids according to the invention include one or more, especially one or two, selective genetic markers, e.g. a marker for yeast and a marker and (except for symmetric two-micron like hybrid vectors) an origin of replication for a bacterial host, especially *Escherchia coli*.

As to the selective gene markers, any marker gene can be used which facilitates the selection for transformants due to the phenotypic expression of the marker gene. Suitable markers are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA3, LEU2, LYS2, HIS3, or TRP1 gene.

As the amplification of the expression plasmids is conveniently done in a prokaryote, such as *E. coli*, a prokaryotic (e.g. *E. coli*), genetic marker and a prokaryotic (e.g. *E. coli*), replication origin are included advantageously. These can be obtained from corresponding prokaryotic plasmids, for example *E. coli* plasmids, such as pBR322 or a pUC plasmid, for example pUC18 or pUC19, which contain both prokaryotic, e.g. *E. coli*, replication origin and genetic marker conferring resistance to antibiotics, such as ampicillin.

Apart from the protein expression cassette, replication origin(s) and genetic marker(s) the expression plasmids according to the invention can contain optionally additional expression cassettes, such as 1 to 3 additional protein expression cassettes. The additional protein expression cassette(s) are identical to or different from each other and are identical to or different from the protein expression cassette already present on the vector.

Isolation of Proteins

The protein can be isolated by conventional means. For example, the first step consists usually in lysing or mechanically breaking the cell wall and removing the cell debris by centrifugation or, in the case of secretory proteins, in separating the cells from the culture fluid by means of centrifugation. The supernatant can be enriched for protein by treatment with polyethyleneimine so as to remove most of the non-proteinaceous material, and precipitation of the proteins by saturating the solution with ammonium sulfate or by extraction with a suitable solvent. Host proteins, if present, can also be precipitated, for example, by means of acidification with acetic acid (for example 0.1%, pH 4–5). Other purification steps include, for example, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, by affinity chromatography, for example with antibodies, especially monoclonal antibodies.

A further embodiment of the invention concerns the use of *Saccharomyces cerevisiae* strain HT393 (DSM 9697) or a derivative thereof for the production of a protein heterologous to yeast in a homogenous form.

BRIEF DESCRIPTION OF THE DRAWINGS

In the following experimental part various embodiments of the present invention are described with reference to the accompanying drawings in which.

Figure 1:
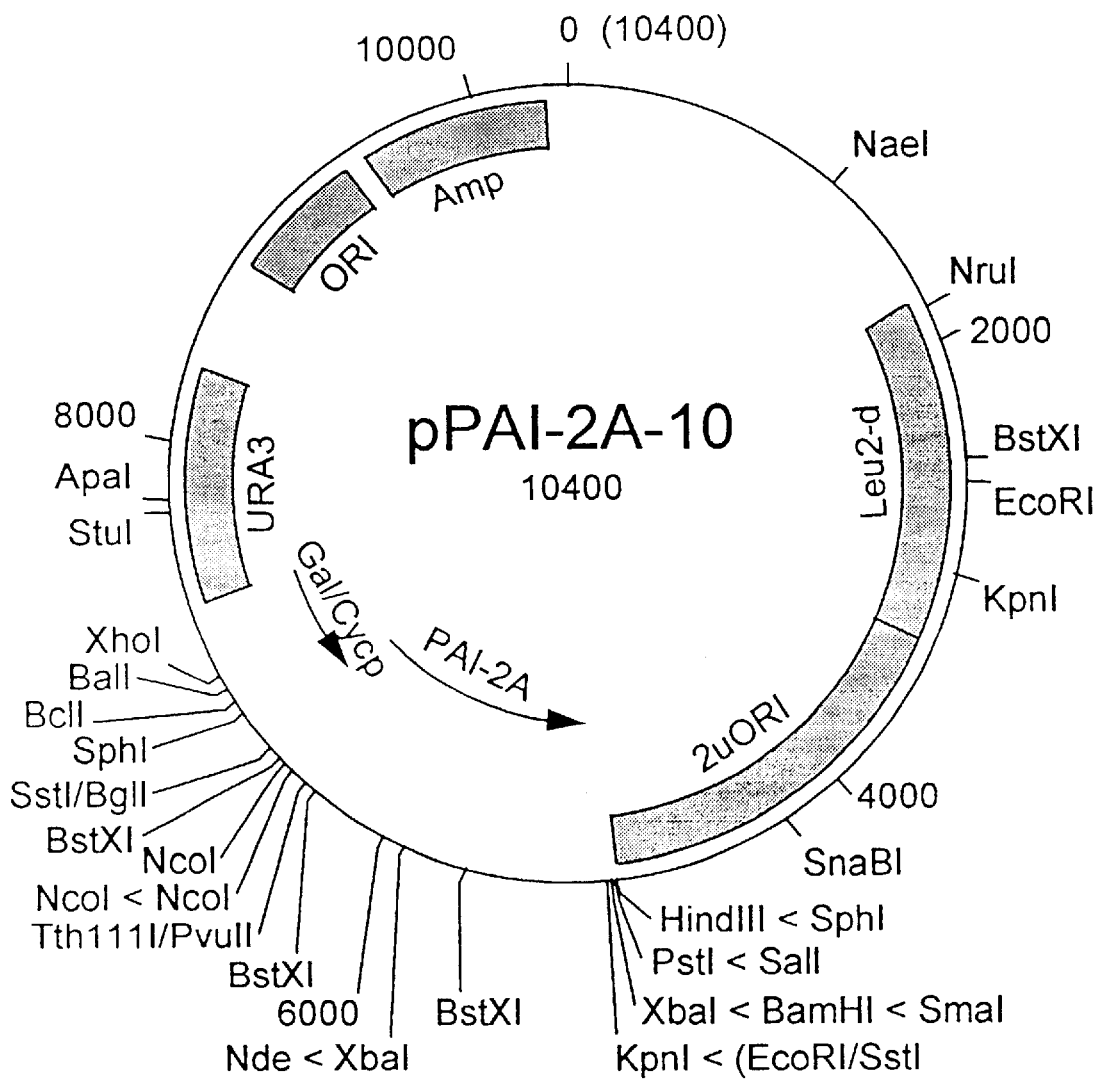
FIG. 1 is a schematic illustration of plasmid pPAI-2A-10.

| | Description of the yeast strain |
|---|---|
| Sc79 | Price et al., Gene (1957), 55, 287–293) |
| XV2181 | Price et al., Gene (1987), 55, 287–293) |
| 150-2B | Baldari et al., EMBO (1987), 6, 229–293) |
| CGY1465 | (Rudolph et al., 3 Cell (1989), 58, 133–145) |
| c13-ABYS-86 | (Heinemeyer et al., EMBO J. (1991), 10, 555–562) DSM 9698 MATα, leu2-3, leu2-112, ura3Δ5, prb1-1, cps1-3, prc1-1, pra1-1, his |
| HT 393 | (Heinemeyer et al., EMBO J. (1991), 10, 555–562) DSM 9697 MATa, leu2-3, leu2-112, ura3Δ5, prb1-1, cps1-3, prc1-1, pra1-1, pra1-1 |

EXAMPLES

All DNA manipulations are -if not otherwise noted- carried out according to standard protocols, e.g. as described in Sambrook et al., *Molecular Cloning: A laboratory manual*, $2^{nd}$ Edn. Cold Spring Harbor Laboratory Press, Cold Spring Harbor N.Y., 1989.

1. Expression of Plasminogen Activator (PAI-2)

1.1 Construction of pMB354

This plasmid is based on the yeast/*E. coli* shuttle vector Yep24 and harbors the ADR2 promoter for the expression of heterologous proteins in *S. cerevisiae*.

The DNA sequence specific for the ADR2 gene is identical with the sequence published by Russell et al. (J. Biol. Chem. (1983), 258, 2674–2682) with the exception that a BamHI and a SalI restriction site are created upstream of the original ATG translation initiation codon of the alcohol dehydrogenase II protein. The mutated EcoRV/XbaI DNA fragment is cloned into pMac 5.8, yielding pMac 5.8-ADR (as described in Stanssus et al., *Nucl. Acids Res.*(1985), 17, 4441–4454), which is digested with SmaI and XbaI. A 1100 bp fragment is isolated therefrom by cutting the plasmid with XbaI and EcoRI. This fragment is cloned into the vector Yep24, cut with NheI and PvuII yielding the new plasmid pMB354.

The relevant section of the cloned ADR2 promoter has the following structure (SEQ ID NO:5):

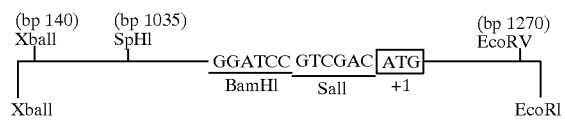

1.2. Isolation of cDNA Coding for PAI-2

The cDNA for PAI-2 is derived from the U937 cell line codes for a protein with 415 amino acids and a predicted Mr. of 46.543 for the unglycosylated protein after removal of the initiator methionine. The protein has three potential N-glycosylation sites (Antalis et al., *Proc. Natl. Acad. Sci. USA 1* (1988), 86, 985–998). A suitable BgIII/EcoRI-DNA fragment comprising PAI-2 is isolated from the plasmid pBTA447 (Antalis et al., *Proc. Natl. Acad. Sci. USA* (1988), 85, 985–989). The protruding BgIII and EcoRI ends are made blunt-ended by the polymerase I Klenow fragment.

This allele type is termed A of PAI-2 (PAI-2A). There exists another allele with three amino acid exchanges at amino acid position $Asn_{120}$ (AAT)→$Asp_{120}$ (GAT), $Asn_{404}$ (AAC)→$Lys_{404}$ (AAG), and $Ser_{413}$ (TCC)→$Cys_{413}$ (TGC), which is termed type B of PAI-2 (PAI-2B).

1.3. Cloning of PAI-1A

PAI-2 expression vectors pPAI-2A-10 and pPAI-2A-20 are based on the plasmid pEMBLyex4 (Cesareni and Murray, *Genetic Engineering* (1989), 9, 135–154). The construction of pEMBLyex4 and the necessary DNA elements are described in detail in this publication.

pEMBLyex4 is cleaved with SacI within the polylinker and the protruding SacI ends are made blunt-ended by polymerase I Klenow fragment prior to ligation with the isolated PAI-2 fragment (see above), resulting in the plasmid pPAI-2A-10 (FIG. 1).

Figure 2:
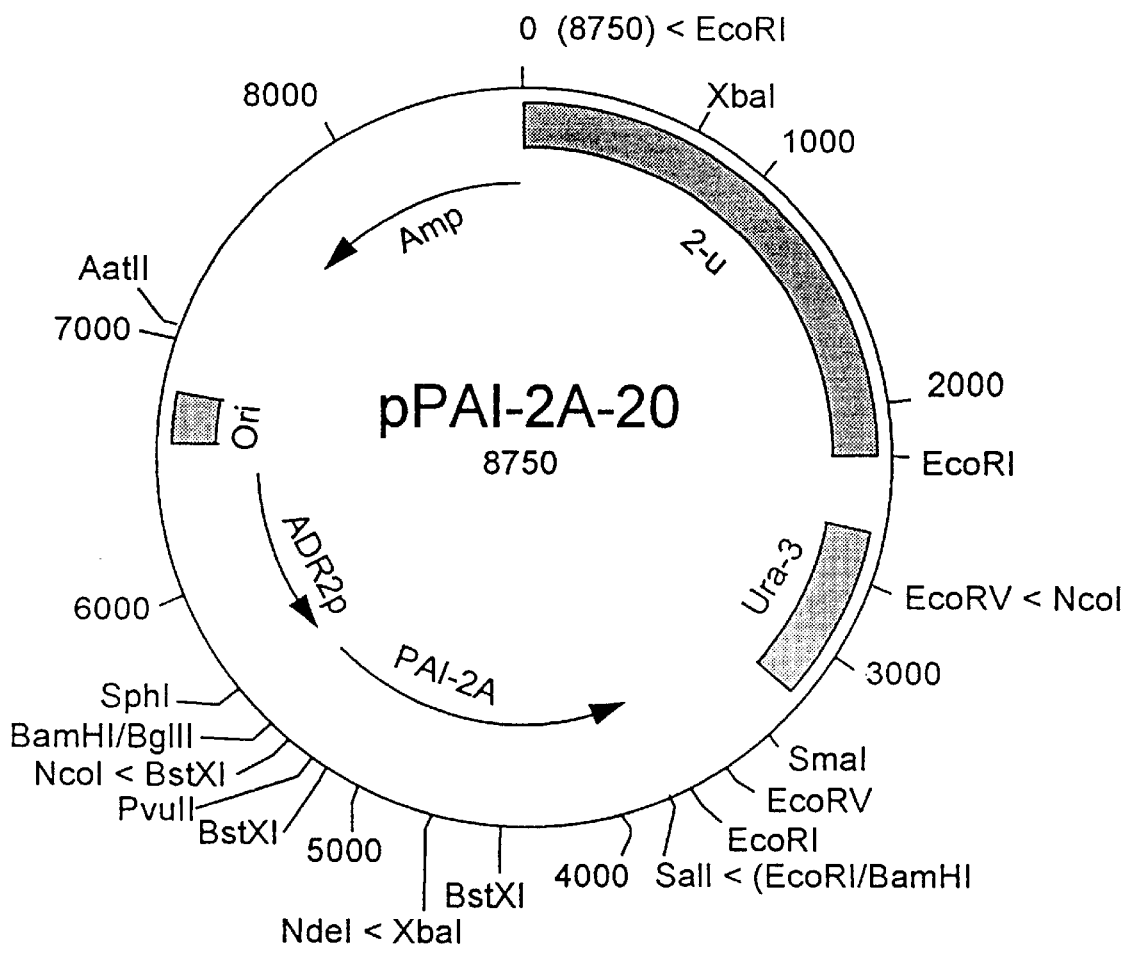
FIG. 2 is a schematic illustration of plasmid pPAI-2A-20.
Figure 3:
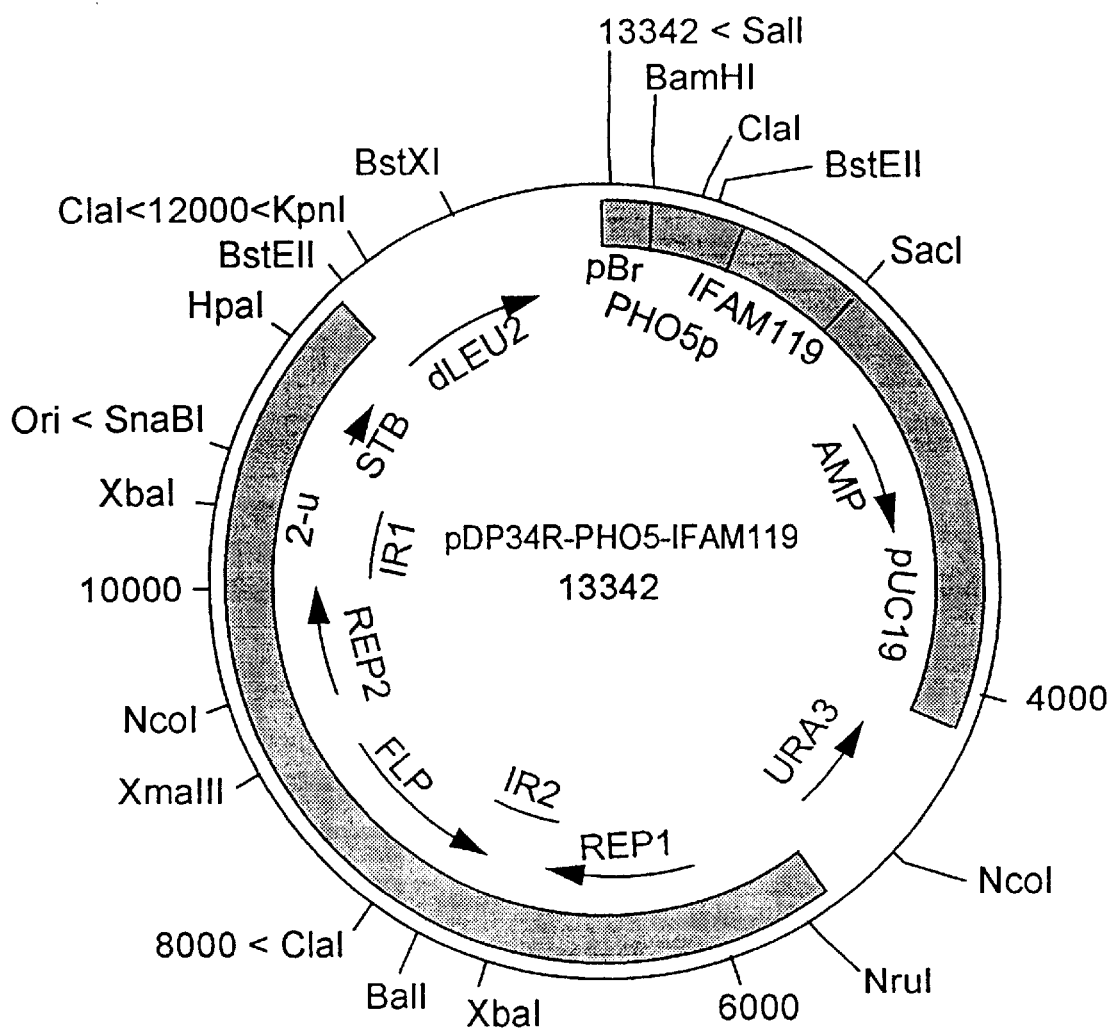
FIG. 3 is a schematic illustration of plasmid pDP34R-PHO5-IFAM119.

In analogy, the PAI-2A cDNA is cloned into the BamHI/SalI site of plasmid pMB354 (example 1.1) to yield pPAI-2A-20 (FIG. 2).

1.4. Cloning of PAI-1B

The DNA coding for PAI-2B is cloned in analogy to the cloning of PAI-2A cDNA into the polylinker of the plasmid pEMBLyex4 (see example 1.3) to yield pPAI-2B-10 and into pMB354 to yield pPAI-2B-20.

1.5. Transformation of Yeasts With pPAI-2A-10 and pPAI-2B-20

The plasmids pPAI-2A-10 and pPAI-2B-20 are transformed into six different strains:

| | |
|---|---|
| Sc79 | Price et al., Gene (1987), 55, 287–293 |
| XV2181 | Price et al., Gene (1987), 55, 287–293 |
| 150-2B | Baldari et al., EMBO (1987), 6, 229–293 |
| CGY1465 | Rudolph et al., Cell (1989), 58, 133–145 |
| c13-ABYS-86 | (Heinemeyer et al., EMBO J. (1991), 10, 555–562) DSM 9698 MATα, leu2-3, leu2-112, ura3Δ5, prb1-1, cps1-3, prc1-1, pra1-1, his |
| HT 393 | (Heinemeyer et al., EMBO J. (1991), 10, 555–562) DSM 9697 MATa, leu2-3, leu2-112, ura3Δ5, prb1-1, cps1-3, prc1-1, pra1-1, pre1-1 |

1.6. Expression of PAI-2A and PAI-2B

PAI-2 can be detected in the soluble fraction of the cell extracts of all strains, but not in the sediment containing insoluble material nor in the culture broth. The expression of PAI-2 is analyzed by Western blotting, ELISA and biological activity testing.

Table 1 documents the expression yields of PAI-2A and PAI-2B in the different strains when cultivated in shaker flasks as described in the references.

TABLE 1

| Strain | Expression of PAI-2A [mg/l] | PAI-2B [mg/l] |
|---|---|---|
| CGY 1465 | nd | 0.1 |
| c13-ABYS-86 | 31.5 | 14.5 |
| HT 393 | 50.8 | 23.7 |
| Sc79 | 0.4 | nd |
| XV 2181 | 14.1 | nd |
| 150-2B | 32.0 | nd | nd = not determined

The strain HT393 is the best producer compared to four other strains when the expression of PAI-2A is under the control of the GAL/CYC1 promoter, yielding 50 mg PAI-2A/l culture broth.

HT393 is also the best host for the expression of PAI-2B under the control of the ADR2 promoter.

In 1 l fermenters, the yields obtained by means of the plasmid pPAI-2A-10 are 310 mg PAI-2/l in strain cl3-ABYS-86 and 680 mg PAI-2/l in strain HT393.

2. Expression of α-interferon B/D Hybrids

2.1 Isolation of the cDNA Clones for α-interferon Subtypes B and D and Construction of B/D Hybrids Human Namalva cells are induced for interferon synthesis by challenging the cells with Newcastle disease virus (NDV 10) under the standard conditions (EP-A-076489). Total mRNA is isolated and fractionated by sucrose density gradient centrifugation as described in EP-A-205404. Enriched fractions are used for cDNA synthesis. Cloning of the poly (dC) extended cDNA is done in the PstI site of the *E. coli* vector pBR322. DNA sequence analysis allows assignment of the genes to the α-interferon subtypes as described by Henco et al. (J. Mol. Biol. (1985) 185, 227–260). Clones coding for polypeptides related to the α-interferon subtypes B and D are isolated.

The presence of common endonuclease restriction sites in subtypes B and D allows the subdividing of the protein coding region into four regions.

Restriction sites of the α-interferon coding region for the separation of these regions:

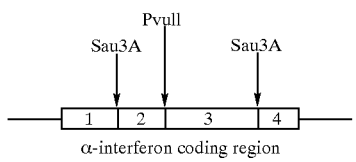

α-interferon coding region

Combination of these subtype B and D regions gives access to 14 different B/D hybrids. The structural arrangement: $B_1\ D_2\ B_3\ B_4$ is an α-interferon of the subtype B with the second region (amino acid residues 61 to 92) replaced by the corresponding region of subtype D. This sequence arrangement is obtained by ligating a restriction fragment containing the first region of the B gene with the rest of the D gene via the first common internal Sau3A restriction site to yield the hybrid $B_1$ $D_2$ $D_3$ $D_4$. The B/D hybrid $B_1$ $D_2$ $B_3$ $B_4$ is obtained by combining the N-terminal half of the $B_1$ $D_2$ $D_3$ $D_4$ gene with the C-terminal half of the B gene ($B_1$ $B_2$ $B_3$ $B_4$) via the common internal PvuII restriction site (EP-A-205404). The B/D hybrid $B_1$ $D_2$ $B_3$ $B_4$is also referred to as IFAM119. The B/D hybrid structure is verified by restriction analysis using restriction endonucleases specific for the subregions of the original B and D genes. Final proof is obtained by DNA sequence analysis. DNA sequence data of the coding region of the hybrid gene $B_1$ $D_2$ $B_3$ $B_4$ are given in SEQ ID NO:1.

2.2. Construction of Expression Plasmid pDP34R/PHO5-IFAM119

Expression of α-interferon B/D is under the control of the repressible promoter of the yeast acid phosphatase gene (PHO5), which is derepressed by low concentrations of inorganic phosphate in the medium.

A BamHI restriction site at position −541 from the ATG of the PHO5 gene and an EcoRI linker inserted at position −8 of the gene allows convenient cloning of the 534 bp BamHI-EcoRI PHO5 promoter fragment. The PHO5 promoter is ligated to the coding sequence of α-interferon B/D via a synthetic oligodeoxynucleotide linker of the following sequence (see SEQ ID NO:1)

```
EcoRI                    DdeI
5' AATTCGACAATGTGTGATCTGCC

3'      GCTGTTACACACTAGACGGAGT
```

The linker (SEQ ID NO:6) provides the EcoRI restriction site for ligation to the PHO5 promoter fragment, four non-transcribed nucleotides, ATG for translation initiation and the genuine α-interferon B/D coding sequence up to the DdeI restriction site at position +14 from the ATG.

The PHO5-IFAM119 expression cassette of plasmid pDP34R/PHO5-IFAM119 consists of the 276 bp SalI-BamHI fragment of pBR322, the 534 bp BamHI/EcoRI PHO5 promoter fragment, the coding sequence of α-interferon B/D (504 bp) and a 181 bp DNA fragment derived from the PHO5 transcription termination region (FIG. 1). The 3' end of the cassette is a HindIII site, which is filled in a reaction with Klenow DNA polymerase and is not cleavable upon cloning of the 1.6 kb SalI-HindIII blunt end expression cassette into the two-micron based yeast vector pDP34 (Hinnen et al. (1989) In Barr et al., (eds.) *Yeast Genetic Engineering.* Butterworths, Boston, pp. 193–213).

The nucleotide sequence of the complete expression cassette of plasmid pDP34R/PHO5-IFAM119 is determined by sequencing on double-stranded DNA using the chain-termination method according to Sanger. The DNA sequence is identical to the expected sequence (SEQ ID NO:1).

Expression plasmid pDP34R/PHO5-IFAM119 comprises the complete yeast two-micron circle, the yeast URA3 gene and the yeast dLEU2 gene. The dLEU2 gene does not have its own promoter (dLEU2≡leu2-d in Erhart et al., *J. Bacteriol.* (1983), 156, 625), therefore transcription of the dLEU2 gene depends on initiation in the 5' upstream two-micron sequences. The plasmid map is given in FIG. 3.

2.3. Expression of the B/D Hybrid pDP34R/PHO5-IFAM119 is introduced into *Saccharomyces cerevisiae* HT 393 in the presence of polyethyleneglycol as described by Hinnen et al., (Proc. Natl. Acad. Sci. USA (1978), 1929). Host strain HT 393 is auxotrophic for leucine and uracil. The expression plasmid contains the dLEU2 and URA3 genes to complement the leucine and uracil auxotrophies of the host. Selection for plasmid-containing transformants is achieved by growth on a leucine supplemented, uracil deficient medium. The expression plasmid pDP34R/PHO5-IFAM119 is stably maintained in the host cell at a high copy number, even under non-selective growth conditions in complex medium.

α-interferon B/D is expressed under the control of the PHO5 promoter, which is induced at low concentrations of inorganic phosphate in the medium.

One single colony of the transformed HT 393 is picked into 10 ml of uracil deficient yeast minimal medium in a shakeflask and grown at 30° C. at 200 r.p.m. for 24 h. These cells are washed with minimal medium and used to inoculate uracil deficient medium for fermentation in a 500 ml shakeflask, in a 2000 ml flask and in a 30 l fermenter for 48 h each. Finally cells are grown for 47 h in a 300 l fermenter using low-$P_i$ complex medium.

The produced interferon accumulates intracellularly in the cytosol of the cell.

2.4. Isolation of α-interferon B/D 5 g cells (from example 2.3) are collected by centrifugation, washed and adjusted with water and buffer (20% NaCl w/w and 8.3% $KH_2PO_4$ w/w) to the following final composition:

| | |
|---|---|
| Wet cell weight: | 60% w/w |
| NaCl: | 0.5 M |
| K-phosphate: | 70 mM. |

The pH is adjusted to pH 7.0 and the cells are broken by a single passage through a Dyno Mill® type KD-5 homogenizer filled with glass beads.

α-interferon B/D is isolated by 2 phase-extraction with a) Extraction into the top phase using a two phase system comprising
   7 parts of a solution of 9.5% K-phosphate and 12.5% NaCl (per weight); and 3 parts PEG 1500
b) Washing of the top phase using a solution of 20% K-phosphate and 5.8% NaCl
c) Back-extraction from the washed phase into the bottom phase using a solution of 18.8% $MgSO_4$ (per weight)
d) and subsequent reversed phase HPLC analysis.

Column: 150×4.6 mm C-18 (Vydac 218TP5415)

Buffer A: 0.1% trifluoro acetic acid in $H_2O$

Buffer B: 80% acetonitrile containing 0.09% trifluoro acetic acid

Flow rate: 2.0 ml/min

Injection vol.: 50 μl

Gradient: 61% solvent B to 100% Solvent B in 35 min.

Retention time for biological active (α-interferon B/D: 22 min±1–2 min.

The amino acid composition of the isolated α-interferon B/D was determined by gas phase hydrolysis and derivatisation of the amino acids with dimethylaminobenzenesulfonyl (DABS; Knecht & Chang, Analyt. Biochem. (1986), 58, 2375–2379) see table 2.

TABLE 2

| Amino Acid | calculated | found |
|---|---|---|
| Ala | 9 | 9.1 |
| Arg | 10 | 10.9 |
| Asp | 15 | 15.3 |
| Cys | 5 | 5.0 |
| Glu | 27 | 29.0 |
| Gly | 2 | 2.1 |
| His | 3 | 3.0 |
| Ile | 10 | 9.1 |
| Leu | 20 | 20.0 |
| Lys | 11 | 9.6 |
| Met | 5 | 4.3 |
| Phe | 10 | 9.6 |
| Pro | 4 | 4.8 |
| Ser | 15 | 13.7 |
| Thr | 6 | 6.8 |
| Trp | 2 | nd |
| Tyr | 5 | 4.9 |
| Val | 7 | 5.7 | nd = not determined

The N-terminal sequence of isolated α-interferon B/D is determined by automated Edman degradation in a gas phase sequencer and detection of the phenylthio-hydantoin amino acids by RP-HPLC. The experimentally determined sequence of the first 20 amino acids corresponds to the predicted sequence (SEQ ID NO:3).

The molar amounts of amino acids per mole of isolated α-interferon B/D determined experimentally by electrospray ionization mass spectroscopy (19566.6×0.27) are in agreement with the calculated values (19568.6).

The specific antiviral activity of isolated α-interferon is $1.5–2.3×10^8$ IU/mg protein (IU: international units) determined in the standard assay according to Rubinstein et al. (J. Virol. (1981), 37, 755) using MDBK cells and VSV (MDBK: Madin Darby bovine kidney; VSV: Vesicular stomatitis virus).

2.5. Comparison With Another Yeast Strain pDP34R/PHO5-IFAM119 is introduced into S. cerevisiae strain cl3-ABYS-86 (parental strain to HT393) and cultured as described above but with additional histidine in the culture broth. The α-interferon produced is isolated as described above (see Table 3).

TABLE 3

| Strain | Expression of interferon [mg/l] |
|---|---|
| cl3-ABYS-86 | 50 |
| HT 393 | 600 |

Strain HT393 transformed with pDP34R/PHO5-IFAM119 shows a ten fold increase in interferon expression compared to the transformed parental strain cl3-ABYS-86 transformed with pDP34R/PHO5-IFAM119.

Deposition of Microorganisms

The following microorganism strains were deposited at the Deutsche Sammlung von Mikroorganismen (DSM), Mascheroder Weg 1B, D-38142 Braunschweig, Germany (accession numbers and deposition dates given):

| | | |
|---|---|---|
| *Saccharomyces cerevisiae* HT 393 | DSM 9697 | 27.01.1995 |
| *Saccharomyces cerevisiae* cl3-ABYS-86 | DSM 9698 | 27.01.1995 |

What is claimed is:

1. A *Saccharomyces cerevisiae* strain HT393 (DSM 9697) cell or a derivative thereof comprising a hybrid vector wherein the vector comprises at least one DNA sequence coding for at least one heterologous protein.

2. The cell of claim 1 wherein the vector is a symmetric two micron-like vector.

3. The cell of claim 1 wherein the at least one DNA sequence is a marker gene.

4. The cell of claim 1 wherein the derivative of HT393 is MATα, leu2-112, ura3Δ5, prb1-1, cps1-3, prc1-1, pra1-1, and pre1-1.

5. The cell of claim 1 wherein the vector is selected from the group consisting of a two-micron plasmid, Yep24 and pEMBLyex.

6. The cell of claim 1 wherein the vector further comprises an expression cassette, the expression cassette comprising a promoter operably linked to a DNA sequence coding for the protein and to a DNA sequence containing at least one transcription termination sequence.

7. The cell of claim 1, wherein the heterologous protein is selected from the group consisting of alpha-interferon, hybrid interferon and an inhibitor of the plasminogen activator.

8. The cell of claim 1, wherein the heterologous protein is hybrid interferon BDBB or the inhibitor of the plasminogen activator PAI-2.

9. The cell of claim 2 wherein the symmetric two micron-like vector is a symmetric two micron-like hybrid vector.

10. The cell of claim 2 wherein the symmetric two micron-like vector is a symmetric two micron-like disintegration vector.

11. The cell of claim 6 wherein the transcription termination sequence is selected from the group consisting of the yeast PHO5, the FLP and the α-factor terminator.

12. The cell of claim 6 wherein the promoter is selected from the group consisting of the PHO5, the ADR2 and the GAL/CYC 1 promoter.

* * * * *